(12) United States Patent
Pathak et al.

(10) Patent No.: US 10,219,930 B2
(45) Date of Patent: Mar. 5, 2019

(54) HIGH AMPLITUDE TREMOR STABILIZATION BY A HANDHELD TOOL

(71) Applicant: Verily Life Sciences LLC, Mountain View, CA (US)

(72) Inventors: Anupam J. Pathak, Mountain View, CA (US); Michael Allen, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 16 days.

(21) Appl. No.: 15/210,267

(22) Filed: Jul. 14, 2016

(65) Prior Publication Data

US 2018/0014958 A1    Jan. 18, 2018

(51) Int. Cl.
*A61F 4/00* (2006.01)
*G05B 13/02* (2006.01)
*A47G 21/02* (2006.01)
*A61B 5/00* (2006.01)
*A61B 5/11* (2006.01)

(52) U.S. Cl.
CPC .............. *A61F 4/00* (2013.01); *A47G 21/02* (2013.01); *A61B 5/1101* (2013.01); *A61B 5/4082* (2013.01); *A61B 5/6887* (2013.01); *G05B 13/021* (2013.01)

(58) Field of Classification Search
CPC ........................................................ A61F 4/00
See application file for complete search history.

(56) References Cited

U.S. PATENT DOCUMENTS

| | | | | |
|---|---|---|---|---|
| 5,828,197 A | * | 10/1998 | Martin | .................. B25J 9/1689 318/560 |
| 2002/0133174 A1 | * | 9/2002 | Charles | .................. A61B 34/70 606/130 |
| 2009/0024142 A1 | * | 1/2009 | Ruiz Morales | .......... B25J 9/041 606/130 |
| 2010/0228362 A1 | | 9/2010 | Pathak et al. | |

(Continued)

OTHER PUBLICATIONS

U.S. Appl. No. 14/627,893; Anupam Pathak, filed Feb. 20, 2015.
(Continued)

*Primary Examiner* — Bruce A Snow
*Assistant Examiner* — Melissa A Hoban
(74) *Attorney, Agent, or Firm* — Christensen O'Connor Johnson Kindness PLLC (57) ABSTRACT

Systems and methods for tracking unintentional high amplitude muscle movements of a user and stabilizing a handheld tool are described. The method may include detecting motion of a housing of the handheld tool when manipulated by a user while the user is performing a task with a user-assistive device attached to an attachment arm of the handheld tool, and storing the detected motion in a memory of the handheld tool as motion data. Furthermore, the method may include controlling a first motion generating mechanism and a second motion generating mechanism by generating a first motion signal and a second motion signal that respectively drive the first motion generating mechanism in a first degree of freedom and the second motion generating mechanism in a second degree of freedom to stabilize motion of the user-assistive device attached to the attachment arm of the handheld tool.

15 Claims, 4 Drawing Sheets

(56) References Cited

U.S. PATENT DOCUMENTS

2013/0297022 A1    11/2013  Pathak
2014/0052275 A1     2/2014  Pathak
2015/0054633 A1     2/2015  Saddik et al.
2015/0300394 A1    10/2015  Pathak

OTHER PUBLICATIONS

U.S. Appl. No. 14/668,516; Anupam Pathak, filed Mar. 25, 2015.
U.S. Appl. No. 14/681,549; Anupam Pathak, filed Apr. 8, 2015.
U.S. Appl. No. 13/250,000; Anupam Pathak, filed Sep. 30, 2011.
PCT/US2017/039077, International Search Report and Written Opinion of the International Searching Authority, dated Sep. 29, 2017, 13 pages.

* cited by examiner

HIGH AMPLITUDE TREMOR STABILIZATION BY A HANDHELD TOOL

TECHNICAL FIELD

This disclosure relates generally to unintentional muscle movements, and in particular but not exclusively, relates to tracking unintentional muscle movements of a user and stabilizing a handheld tool while it is being used by the user.

BACKGROUND INFORMATION

Movement disorders are often caused by chronic neurodegenerative diseases such as Parkinson's Disease ("PD") and Essential Tremor ("ET"). Both of these conditions are currently incurable and cause unintentional muscle movements or human tremors—uncontrollable rhythmic oscillatory movements of the human body. In many cases human tremors can be severe enough to cause a significant degradation in quality of life, interfering with daily activities/tasks such as eating, drinking, or writing.

Currently, persons with chronic neurodegenerative diseases are typically medicated with drugs that vary in effectiveness. The alternative to pharmacological treatment is brain surgery, such as deep brain stimulation (DBS) surgery. Similar to pharmacological treatments, DBS surgery varies in its effectiveness while being invasive and dangerous. Both forms of treatment are therefore non-optimal for treating persons with chronic neurodegenerative diseases, especially with respect to performing daily activities.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus, system and process for tracking unintentional high amplitude muscle movements of a user while using a handheld tool and stabilizing the handheld tool while the handheld tool is used to perform an ordinary activity, are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1A:
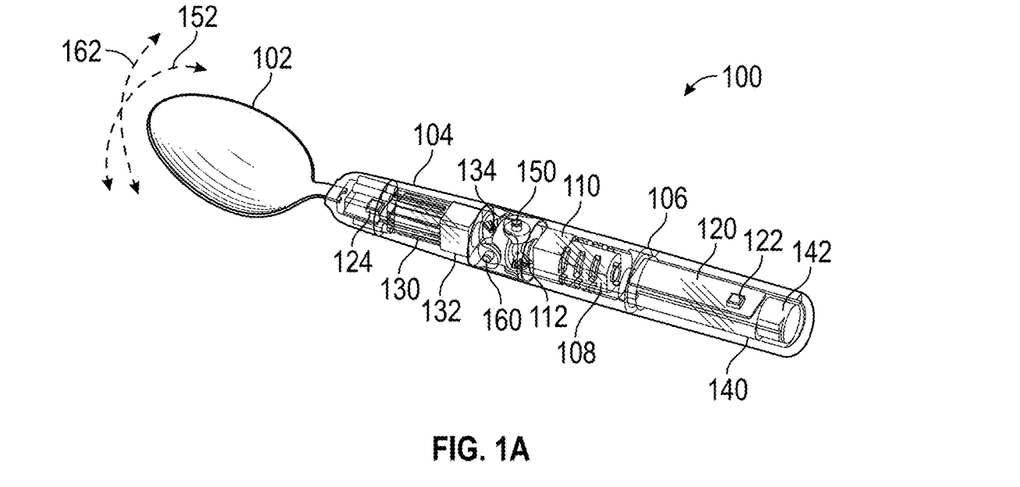
FIG. 1A is a perspective view illustration of a handheld tool that tracks unintentional muscle movements and performs high amplitude motion stabilization, in accordance with an embodiment of the disclosure.

FIG. 1A illustrates a handheld tool 100 that tracks unintentional high amplitude muscle movements and performs motion stabilization, in accordance with an embodiment of the disclosure. Handheld tool 100 is capable of detecting and compensating for unintentional high amplitude muscle movement (e.g. tremors). In one embodiment, the muscle movements are high amplitude when they occur in a range of approximately 1-2 centimeters about a central point of the handheld tool, although unintentional high amplitude muscle movements may be as large as 8-10 centimeters about a central point of the handheld tool. In the embodiments discussed herein, the handheld tool 100 tracks these unintentional high amplitude muscle movements, and stabilizes (i.e., centers) a position of implement 106 in spite of the unintentional high amplitude muscle movements while implement is being used by a user.

Accordingly, the illustrated embodiment of handheld tool 100 includes a tremor tracking module 120 for measuring and tracking user tremors, as well as two or more sensors (e.g., sensor 122 and 124) for providing signals to the tremor tracking module 120 for compensating for those same tremors, as discussed herein. These subsystems may have distinct components, or share some components such as power systems, memory, and may even share one or more sensors.

Handheld tool 100 includes a housing 106, which functions as a handle enabling a user to hold handheld tool 100. Handheld tool 100 also includes an attachment arm 104 coupled to the housing 106 via motion generating mechanisms, as discussed in greater detail below. Attachment arm 104 is configured to accept an implement 102 (e.g., a user-assistive device, such as a spoon in the illustrated embodiment) to its end distal from housing 106. In one embodiment, attachment arm 104 is integrated with a specific type of implement 102 (e.g., the spoon as illustrated). In other embodiments, attachment arm 104 can receive a variety of different implements 102 in a variety of ways including but not limited to a friction, snap, magnet, screw, or other form of locking mechanism. FIG. 1C is a perspective view of one embodiment of the implement 102 detached from the attachment arm 104 of handheld tool 100, such that a plurality of different implements can be selectively attached to attachment arm 104.

Handheld tool 100 includes tremor tracking module ("TTM") 120 for measuring and tracking tremors, such as unintentional high amplitude muscle movements of a user, as well as for controlling stabilization performed by the handheld tool using a first motion generating mechanism (e.g., the first actuator 108, first gear reduction unit 110, and first gearing unit 112) and a second motion generating mechanism (e.g., the second actuator 130, second gear reduction unit 132, and second gearing unit 134), discussed in greater detail below. In embodiments, the attachment arm 104 is coupled with the housing 106 via the coupling of the first motion generating mechanism with the second motion generating mechanism. Furthermore, one or more components of TTM 120 are rigidly attached to housing 106 to measure and track tremors of the handle that the user holds. FIG. 1A illustrates TTM 120 as a single component within housing 106; however, in other embodiments, TTM 120 includes several functional items that may assume a variety of different form factors and may further be spread throughout housing 106, such as within attachment arm 104.

The illustrated embodiment of handheld tool 100 further includes at least two motion sensors (e.g., a first motion sensor 122 placed along or within body and a second motion sensor 124 placed along or within attachment arm 104). The motion sensors 122 and 124 respectively measure movements of housing 106 and attachment arm 104, to enable TTM 120 to determine movements of housing 106 and attachment arm 104 relative to one another. The sensor 122 sends motion signals back to TTM 120 so that TTM 120 can determine, in real time or near real time, direction, speed, and magnitude of unintentional high amplitude muscle movements of a user using handheld tool 100. These measured movements are provided to TTM 120 to enable TTM 120 to provide motion signals that drive the first and second motion generating mechanisms to stabilize the implement 102 despite the user's unintentional high amplitude muscle movements. In one embodiment, the motion sensors 122 and 124 are sensors including but not limited to one or more of an accelerometer, gyroscope, or combination of the two. In another embodiment, each of motion sensor 122 and 124 is a inertial measuring unit.

Handheld tool 100 further includes a portable power source 140 to power the TTM 120, actuator 108, and actuator 130. The portable power source 140 can include one or more rechargeable batteries. In embodiments, the rechargeable batteries of portable power source 140 may be recharged via charging interface 142 to a charging power source, where charging interface 142 couples portable power source 140 to the charging power source via an indicative, wired, or other form of connection. Furthermore, power source 140 may utilize other options including but not limited to a solar panel, primary batteries, etc.

In one embodiment, the first motion sensor 122 and second motion sensor 124 are inertial motion sensors respectively distributed in housing 106 and attachment arm 104. In another embodiment, the second motion sensor 124 can be an accelerometer with or without a gyroscope. In one embodiment, the first motion sensor 122 is responsible for measuring movements of the housing 106 and the second motion sensor 124 is responsible for measuring movements of the attachment arm 104. The first and second motion sensors 122 and 124 provide motion signals, indicative of the measured movements, to TTM 120 for determining the motion of the housing 106 as well as the relative motions of the housing 106 and the attachment arm 104. In embodiments, one or more of the components for tracking tremor motions and/or performing motion stabilization may be omitted and/or positions of sensors changed while still implementing the tremor tracking and motion stabilization functionality disclosed herein. As examples, rotary encoders, potentiometers, or other position tracking devices placed on the joints of movement of the handheld tool 100, and a single motion sensor can be employed either in the tip (e.g., attachment arm 104 or implement 102) or housing 106. In these embodiments, the combination of sensors and placement on handheld tool 100 enable TTM 120 to infer (through device kinematics) where attachment arm 104 and housing 106 are, and their positions relative to each other, for tremor tracking and motion compensation purposes.

The first motion sensor 122 and second motion sensor 124 detect unintentional muscle movements and measure signals related to these unintentional muscle movements that are created when a user adversely affects motion of implement 102 (e.g., as a result of unintentional high amplitude muscle movements). These sensors also detect the motion of the stabilized output relative to the housing 106. In one embodiment, the first motion sensor 122 detects movements of the housing 106, although sensor 124 could also be used for detecting movements of the housing 106. Furthermore, the combined measurements of the sensors 122 and 124 enable movements of the housing 106 and implement 102 relative to one another to also be detected. TTM 120 sends voltage commands in response to the detected motions to at least one of actuator 108 and actuator 130. The voltage commands are chosen by TTM 120 to generate a complementary motion to the detected motions of housing 106. In one embodiment, the complementary motion is a positioning of attachment arm 104 upon jointly driving actuator 108 and actuator 130 to stabilize implement 102 (e.g., maintain implement 102 in a centered position relative to the user's tremors or unintentional muscle movements effecting motion of the handle 106). The voltage commands drive one or more of actuator 108 and actuator 130 to generate motion of the attachment arm 104 and therefore the implement 102 in a direction opposite to the detected user motions. Furthermore, the voltage commands further drive one or more of actuator 108 and actuator 130 to generate a motion of equal magnitude of the detected user motion. The voltage commands of TTM 120 therefore control motion of the implement 102 by jointly driving the motion generating mechanisms to cancel out the user's unintentional high amplitude motion thereby stabilizing the implement 102 relative to motion of the housing 106 by a user.

In one embodiment, the handheld tool 100 includes a first motion generating mechanism having the first actuator 108, first gear reduction unit 110, and first gearing unit 112. In response to a first set of voltage commands of the TTM 120, the first actuator 108 drives the first gearing unit 112 through the first gear reduction unit 112 to move the attachment arm 104 and the attached implement 102 on pivot 150 in a first degree of freedom 152 relative to the housing 106. Similarly, in response to a second set of voltage commands of the TTM 120, the second actuator 130 drives the second gearing unit 134 through the second gear reduction unit 132 to move the attachment arm 104 and the attached implement 102 on pivot 160 in a second degree of freedom 162 relative to the housing 106. The first degree of freedom and the second degree of freedom are different, and in one embodiment, the first and second degrees of freedom are perpendicular to one another (e.g., 90 degrees different from one another). In embodiments, the first and/or second motion generating mechanisms employ gearing units that translate motion to orthogonal directions relative to the motions generated by their respective actuators. Such a translation of motion of the actuators to an orthogonal direction can be achieved through bevel gearing units, such as those illustrated in FIGS. 1A-1C. Other types of gearing or combinations of types of gearing, such as work gearing units, a work gearing unit and a bevel gearing unit, etc., capable of translating the actuators' 108 and 130 motions to orthogonal directions can be employed by the handheld tool 100 consistent with the discussion herein.

Figure 1B:
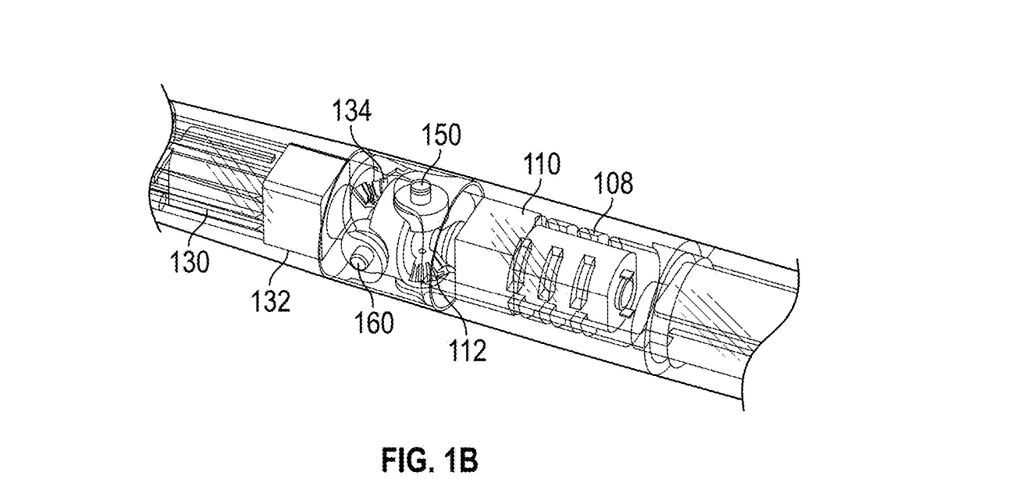
FIG. 1B is a perspective view illustration of motion generating mechanisms of a handheld tool that tracks unintentional muscle movements and performs high amplitude motion stabilization, in accordance with an embodiment of the disclosure.
Figure 1C:
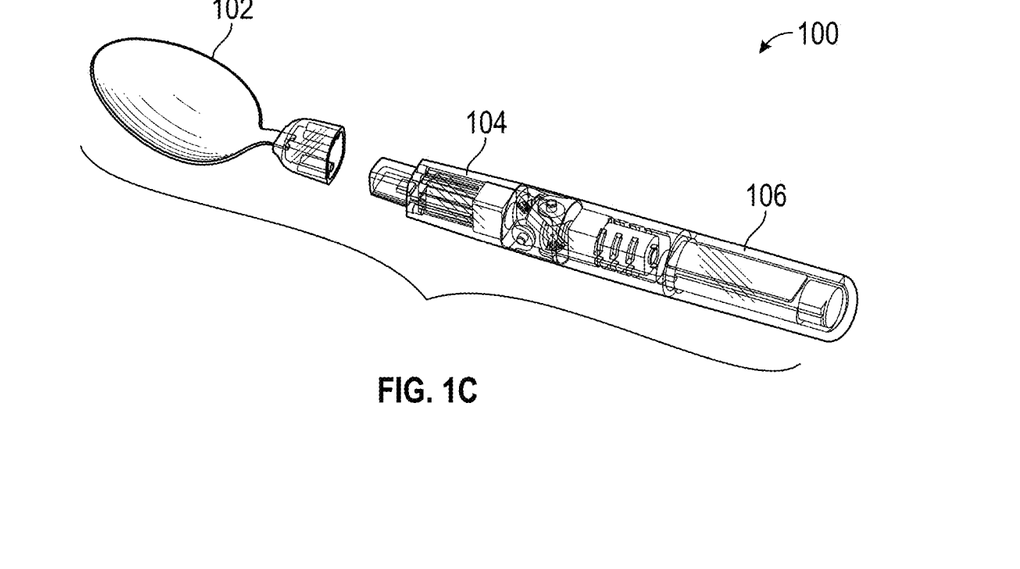
FIG. 1C is a perspective view illustration of a handheld tool that tracks unintentional muscle movements and performs high amplitude motion stabilization with a user-assistive device detached from the handheld tool, in accordance with an embodiment of the disclosure.

FIG. 1B illustrates a zoomed in perspective view of the first and second motion generating mechanisms, including the first actuator 108, first gear reduction unit 110, first gearing unit 112 that moves an attachment arm in a first degree of freedom through pivot 150, as well as the second actuator 130, second gear reduction unit 132, second gearing unit 134 that moves the attachment arm in a second degree of freedom through pivot 160. As noted above, the attachment arm of the handheld tool is coupled with the housing via the coupling of the first motion generating mechanism with the second motion generating mechanism, such as by having pivots 150 and 160 share a common, or connected, structure. Although the illustrated motion generating mechanisms utilize actuators that drive the movement of the attachment via shell gearing units and pivots, in embodiments, other types of actuators and drive units (e.g., direct drive actuators) could be used in the motion generating mechanisms consistent with the discussion herein.

Returning to FIG. 1A, in embodiments, the motions of the attachment arm 104 and the attached implement 102 in the first and second degrees of freedom enable TTM 120 to stabilize implement 102 in 360 degrees of freedom (e.g., responsive to any pattern and direction of unintentional muscle movements of a user). Furthermore, in embodiments, each of actuators 108 and 130 drive its respective gearing unit 112 and 134 a distance in the range of 2 cm from peak to peak in its respective degree of freedom, and up to a potential range of 10 cm from peak to peak in its respective degree of freedom. That is, voltage commands from TTM 120 that jointly drive a position of attachment arm 104 and the attached implement 102 via control of actuators 108 and 130 provide motion stabilization of implement 102 (e.g., centering of implement 102 at a single point in space) up to a total range of 10 cm about the stabilization point in 360 degrees of freedom. Such a range of motion stabilization, provided in real time as a user uses handheld tool 100, enables the stabilization of implement 102 in a range suitable for cancelling unintentional high amplitude muscle movements of a user.

In embodiments, the first actuator 108 and the second actuator 130 are each disposed within handheld tool in an orientation parallel to housing 106. That is, the first actuator 108 is parallel and in-line with the body of the housing 106, and the second actuator 130 is parallel and in-line with the body of the body of the attachment arm 104. For example, actuators 108 and 130 may be substantially cylindrical in shape, and placement of the actuators within and in line with the housing 106 and attachment arm 104 ensures that the diameter of the attachment arm and housing can be reduced to a minimum that accommodates the components of the handheld tool.

Then, in order to provide movement of the implement 102 in the first and second degrees of freedom, the actuators drive their respective gearing units 112 and 134 to control motions of the attachment arm 104 and the attached implement 102. Furthermore, by orienting the actuators 108 and 130 in this direction, a form factor of the housing 108 can be reduced, for example, as compared to the form factor needed when an actuator is perpendicular (or another orientation) relative to a handheld tool's housing. Beneficially, reducing the form factor of the housing ensures the handheld tool 102 more closely resembles a tradition version of the handheld tool, thereby making the handheld tool easy to use. Additionally, users that use the handheld tool 102 which more closely resembles a tradition version of the handheld tool are more comfortable using such a tool, as it is more familiar and does not resemble a specialized/assistive device.

Figure 2:
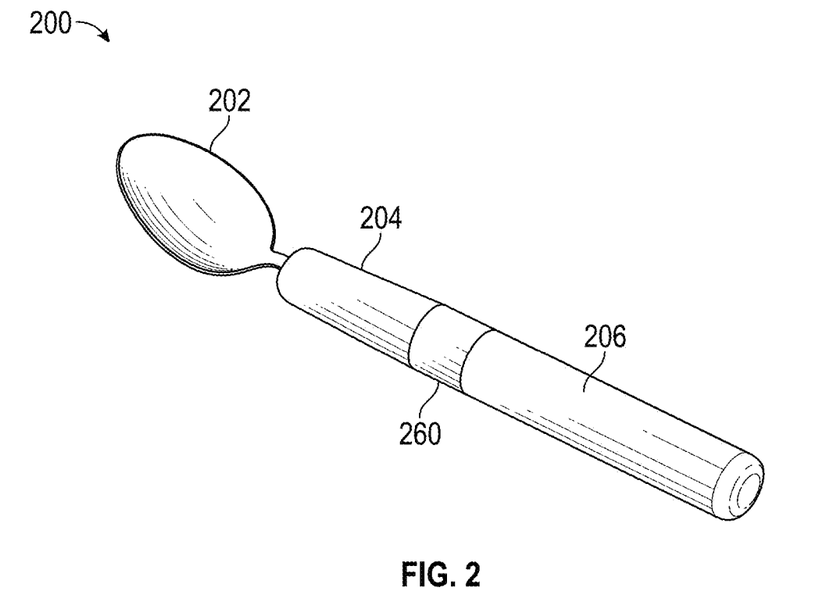
FIG. 2 is a perspective view illustration of a sealed handheld tool that tracks unintentional high amplitude muscle movements and performs motion stabilization, in accordance with an embodiment of the disclosure.

FIG. 2 is a perspective view illustration of another embodiment, of a handheld tool. In the embodiment of FIG. 2, a sealed handheld tool 200 that tracks unintentional high amplitude muscle movements and performs motion stabilization, in accordance with an embodiment of the disclosure, is illustrated. The sealed handheld tool 200 includes a housing 206, attachment arm 204, and implement 202 coupled to the attachment arm 204. Furthermore, handheld tool 200 is similar to handheld tool 100 discussed above, in that it includes a power source, control circuit (e.g., a TTM), a plurality of motion sensors to track movements of the handheld tool 200 and attachment arm 204/implement 202, motion generating mechanisms, etc., each configured to perform the functions discussed above in FIG. 1A.

In one embodiment, handheld tool 200 is sealed to provide a moisture/debris resistance and/or proofing of the motion generating mechanism portions of the handheld tool 200. In one embodiment, a barrier, such as a flexible sleeve 260, is fixed to the housing 206 and the attachment arm 204. In one embodiment, the flexible sleeve 260 may be a flexible tube constructed of moisture impermeable silicon, plastic, nylon, rubber, etc. Such a flexible sleeve will protect the gearing units, gear reduction units, and actuators from unwanted moisture and/or debris that may be encountered during use of the implement (e.g., while a user is eating with a spoon implement attached to the handheld tool 200), as well as from moisture and debris working its way into the housing 206 and/or attachment arm 204 portions of handheld tool 200. Beneficially, by providing protection of the motion generating mechanism portions of the handheld tool 200, the tool becomes more sturdy and robust for everyday use.

Returning to FIG. 1A, in one embodiment, the voltage commands generated by TTM 120 drive the actuators, which may be motors that turn their respective gear units. In embodiments, the voltage commands/signals turn the gearing units in a coordinated manner to generate an equal and opposite motion of the attachment arm 104 and the attached implement 102 to the direction of detected unintentional high amplitude muscle movements of a user. This cancellation maintains and stabilizes a position of the implement 102 relative to the housing 106.

One of ordinary skill in the art readily recognizes that a system and method in accordance with the present disclosure may utilize various implementations of TTM 120 that would be within the spirit and scope of the present disclosure. In one embodiment, TTM 120 comprises an electrical system capable of producing an electrical response from sensor inputs such as a programmable microcontroller a field-programmable gate array (FPGA), an application specific integrated circuit ("ASIC"), or otherwise. In one embodiment, TTM 120 comprises an 8-bit ATMEGA series programmable microcontroller manufactured by Atmel due to its overall low-cost, low-power consumption and ability to be utilized in high-volume applications.

One of ordinary skill in the art will readily recognize that an apparatus, a system, or method as described herein may be utilized for a variety of applications. For example, various different implements 102 may include user-assistive devices such as a manufacturing tool, a surgical tool, a kitchen utensil (e.g., fork, knife, spoon), a sporting tool, a yard tool, a grooming tool (e.g., comb, nail clippers, tweezers, make-up applicator, etc.), or a dental hygiene tool (e.g., toothbrush, flossing tool, etc.). The different implements may be detachably attached to the handheld tool 100, or may be integrated therewith. Thus, handheld tool 100 may be useful in not only improving the quality of life for the multitudes of individuals suffering from neurological motion disorders, but also in assisting in a variety of applications where physiological tremor is an issue including but not limited to manufacturing, surgical and public safety applications.

Figure 3:
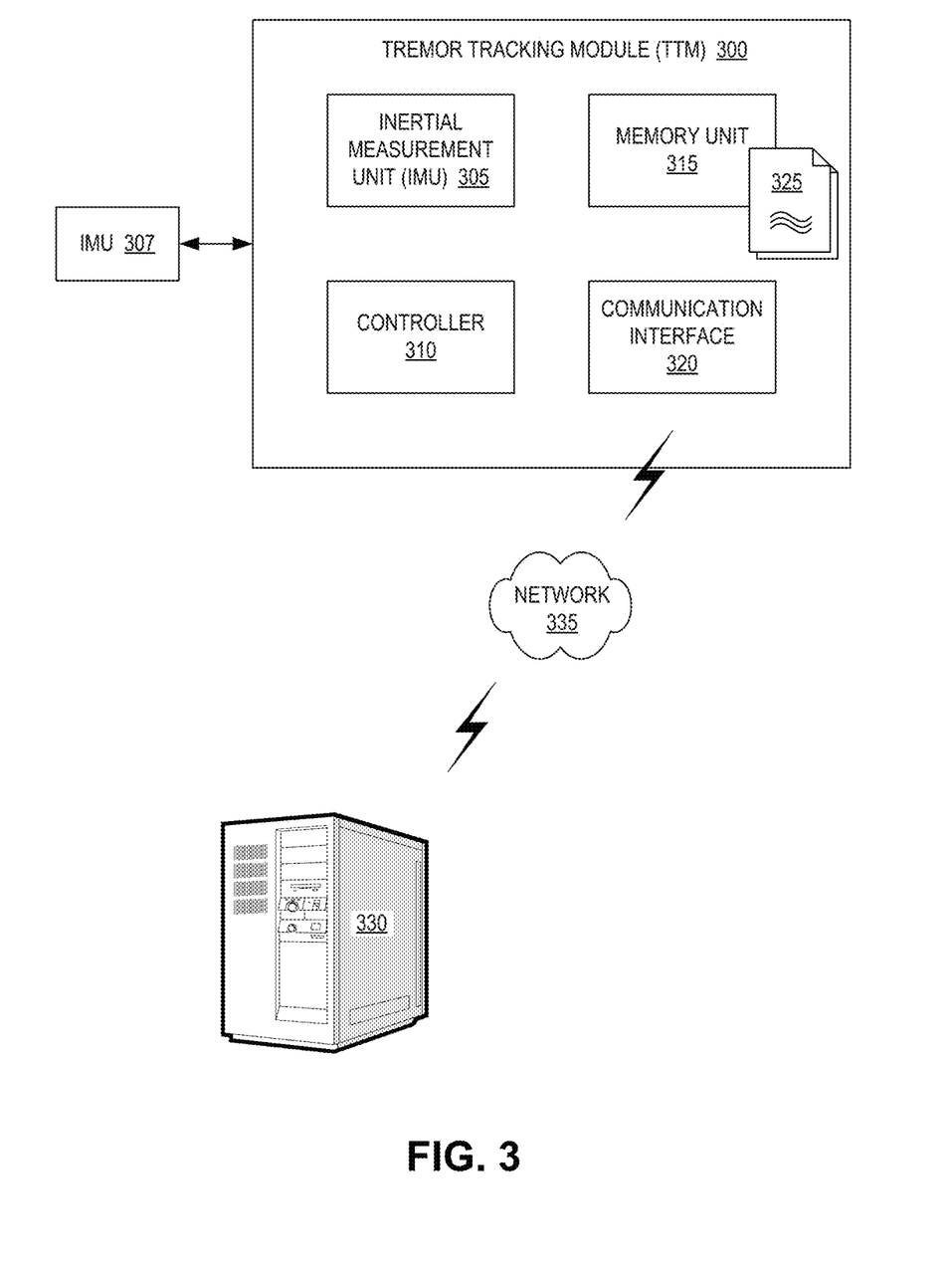
FIG. 3 is a functional block diagram illustrating a tremor tracking module, in accordance with an embodiment of the disclosure.

FIG. 3 is a functional block diagram illustrating a TTM 300, in accordance with an embodiment of the disclosure. TTM 300 is one possible implementation of TTM 120 illustrated in FIG. 1A, and TTM 220 illustrated in FIGS. 2A and 2B. The illustrated embodiment of TTM 300 includes an inertial measurement unit ("IMU") 305, an IMU 307 communicably coupled with TTM 300, a controller 310, a memory unit 315, and a communication interface 320.

In one embodiment, IMU 305 is disposed in rigid contact with the housing of a handheld tool to directly measure the tremor motions of the handle and by extension the tremor motions of the user's hand. IMU 307 is disposed in, or in contact with, an attachment arm of the handheld tool and measures motions of the attachment arm. In one embodiment, IMU 305 and IMU 307 have a known orientation relative to one another (e.g., based on a known orientation of the attachment arm to the handle of the handheld tool). TTM 300 facilitates the measurement of human tremors using IMU 305, and optionally IMU 307, while a user is performing an everyday task, such as eating or grooming (e.g., applying makeup). This is an important distinction over conventional in-clinic evaluations that simply measure the tremor of a hand that a patient is attempting to hold steady. Measurement and tracking of tremors while the patient is performing an everyday task measures the condition under real-world scenarios that are most adversely impacted by human tremors. Accordingly, TTM 300 can be embedded within everyday items or tools that are used routinely by patients to accurately measure and track their condition. This can lead to improved evaluations.

Not only can TTM 300 of a handheld tool measure and track human tremors during a routine task, but it can conveniently do so over a period of time to obtain a more reliable dataset for statistical analysis. Furthermore, the handheld tool including TTM 300 can be used at home where the user is more relaxed and under less stress than a formal evaluation in a practitioner's office. Data collection within the home environment along with larger datasets than can be obtained in-clinic, can provide more reliable data for evaluation of a patient's symptoms. Improved evaluation and diagnosis of the patient's tremors facilitate improved treatments and interventions of the various diseases and the conditions that cause human tremors.

IMUs 305 and 307 may be implemented using a variety of devices that measure motions of the handle of handheld tool 100, motions of the attachment arm of handheld tool 100, and motions of the handle and attachment arm relative to one another. For example, IMUs 305 and 307 may include one or more accelerometers that measure linear accelerations. In one embodiment, IMUs 305 and 307 includes accelerometers capable of measuring translational accelerations of the handle and attachment arm in three orthogonal dimensions (e.g., x, y, and z dimensions). In one embodiment, IMUs 305 and 307 includes a gyroscope to measure rotational motions (e.g., angular velocity about an axis) of the handle and attachment arm of handheld tool 100. In various embodiments, the gyroscope may be capable of measuring the rotational motions about one, two, or three orthogonal rotational axes. In one embodiment, IMUs 305 and 307 includes a magnetometer to measure motions of the handle and attachment arm relative to a magnetic field (e.g., Earth's magnetic field or other externally applied magnetic field). In various embodiments, IMUs 305 and 307 may include various combinations of some or all of the above listed motion measuring devices. Furthermore, these motion sensors may be disposed together in an IMU on a common substrate that is rigidly attached to housing or attachment arm, or disposed throughout. In one embodiment, by using the combined motion measurements of IMU 305 and 307, other motion sensing devices (e.g., contactless position sensors) need not be deployed within a handheld tool, thereby simplifying the construction of the handheld tool, lowering the cost of the handheld tool, reducing power consumption by the handheld tool, simplifying motion stabilization control performed by controller 310, etc.

Controller 310 is communicatively coupled to IMUs 305 and 307 and memory unit 315 to read motion data output from IMUs 305 and 307 and store the motion data into memory unit 315. The motion data is collected over a period of time. For example, the motion data may be collected while the user performs an individual task, over the course of a day, a week, or other period of time. The collected motion data stored in memory unit 315 forms a motion log 325. In one embodiment, motion log 325 may contain enough information about the user's motions (linear accelerations, rotational velocities, durations of these accelerations/velocities, orientation relative to a magnetic field, etc.), based upon the motion data output from IMUs 305 and 307, to recreate those motions using motion log 325. In one embodiment, motion log 325 may also record date/time stamps of when the motion data was collected and even include identifiers indicating the type of implement 102 that was attached to the handheld tool 100 when the motion data was collected. The type identifier provides an indication of the activity (e.g., eating with a fork, knife, or spoon, etc.) being performed by the user when the motion data was collected. This activity information and time/date stamps may be useful for the practitioner when evaluating the patient's motion log 325 to determine if the patient's tremors correlate to particular activities or time of day. In yet other embodiments, motion log 325 may also record battery voltage as a function of date/time, which may be used to analyzing system performance and battery usage. Tracking battery voltage is a sort of proxy for the amount of effort exerted by actuators 108 and 130 to stabilize implement 102. As such, tracking battery voltage or battery consumption correlates to the degree of a user's tremors since battery consumption will rise with increased tremors.

In one embodiment, controller 310 further provides signals to actuators 108 and 130 for controlling motion of the attachment arm 104 and thus the implement 102. As discussed herein, the signals generated by controller 310 cause actuators 108 and 130 to jointly move the attachment arm 104 and the implement 102 via gearing units 112 and 134 in equal and opposite directions as detected user motions of housing 106. As discussed herein, the movement of implement 102 occurs through the combined/joint movement of attachment arm 104 by actuators 108 and 130, providing stabilization for 360 degrees of user movement. That is, based on a known orientation of the housing to the implement, motion data collected by the IMUs 305 and 307 enables controller 310 to generate signals that simultaneously drive the first and second actuators in corresponding first and second degrees of freedom to stabilize the implement during high amplitude motion of the handle of a handheld tool.

Controller 310 may be implemented with a programmable microcontroller, an FPGA, an ASIC, or other devices capable of executing logical instructions. The logical instructions themselves may be hardware logic, software logic (e.g., stored within memory unit 315 or elsewhere), or a combination of both. Memory unit 315 may be implemented using volatile or non-volatile memory (e.g., flash memory).

Communication interface 320 is communicatively coupled to output the motion log 325 from memory unit 315 to remote server 330 via network 335 (e.g., the Internet). In one embodiment, communication interface 320 is a wireless communication interface (e.g., Bluetooth, WiFi, etc.). For example, communication interface 320 may establish a wireless link to a user's cellular phone which delivers motion log 325 to server 330 via an installed tremor tracking application. The application may enable the user to control privacy settings, add comments about their usage of handheld tool 100, setup automatic periodic reporting of motion log 325, initiate a one-time reporting of motion log 325, determine a predominant direction of unintentional muscle movements detected by TTM 300, receive instructions or an indication as to how to set implement 102 relative to housing 106 to enable motion stabilization in a single degree of freedom, along with other user functions. In yet another embodiment, communication interface 320 may be a wired communication port (e.g., USB port). For example, when the user connects handheld tool 100 to a charging dock to charge power source 122, communication interface 320 may also establish a communication session with remote server 330 for delivery of motion log 325 thereto.

Figure 4:
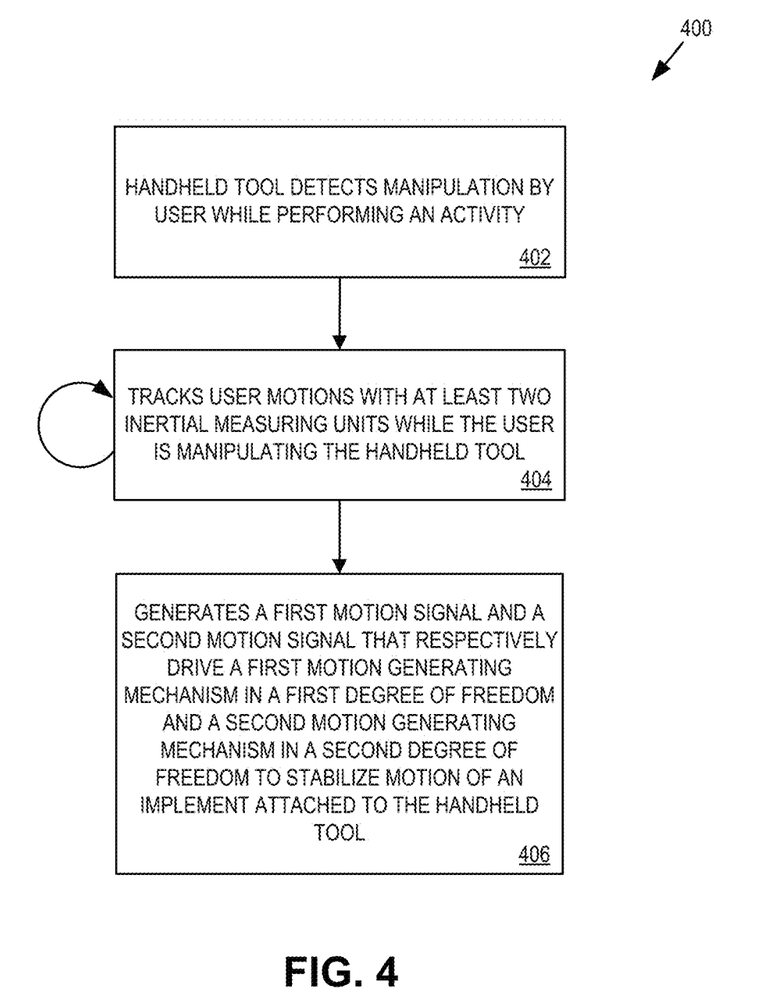
FIG. 4 is a flow chart illustrating a process for tracking unintentional muscle movements of a user while using a handheld tool and performing high amplitude motion stabilization by the handheld tool, in accordance with an embodiment of the disclosure.

FIG. 4 is a flow chart illustrating a process 400 for tracking unintentional muscle movements of a user while using a handheld tool and performing high amplitude motion stabilization by the handheld tool, in accordance with an embodiment of the disclosure. The process 400 is performed by processing logic that may comprise hardware (circuitry, dedicated logic, etc.), software (such as is run on a general purpose computer system or a dedicated machine), firmware, or a combination. In one embodiment, the process is performed by a tremor tracking module of a handheld tool (e.g., TTM 120 or 220). Furthermore, the order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

The process begins by handheld tool detecting manipulation by a user while performing an activity (processing block 402). In one embodiment, the user uses the handheld tool (e.g., handheld tool 100 or 200) to perform a task or activity, such as a routine everyday activity including eating or grooming. Of course, handheld tool may also be used for other non-routine activities, as described above. In one embodiment, handheld tool detects the manipulation by detecting movement of the handheld tool based on measurements collected from at least one sensor of the handheld tool.

Processing logic tracks user motions with at least two inertial measuring units while the user is manipulating the handheld tool (processing block 404). In one embodiment, one of the inertial measuring units may include the sensor used to detect manipulation of the handheld tool by the user discussed above in processing block 402. In one embodiment, processing logic detect motion of the handheld tool with the at least two inertial measuring units, and thus movement of a user. Processing logic continues to track user motions while the handheld tool is being manipulated by the user.

Processing logic generates a first motion signal and a second motion signal that respectively drive a first motion generating mechanism in a first degree of freedom and a second motion generating mechanism in a second degree of freedom to stabilize motion of an implement attached to the handheld tool (processing block 406). As discussed herein, implement may be attached to an attachment arm of a handheld tool, as discussed above. In one embodiment, the first degree of freedom and the second degree of freedom are different, such as perpendicular to one another. Thus, the combined and simultaneous driving of the motion generating mechanisms in their respective degrees of freedom enables stabilization of the implement in 360 degrees of freedom.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A handheld tool, comprising:
   a housing;
   an attachment arm coupled with the housing ;
   a first motion generating mechanism mechanically coupled to a second motion generating mechanism through first and second pivots, wherein the first motion generating mechanism is mounted to the housing while the second motion generating mechanism is rigidly mounted to the attachment arm, and wherein the first motion generating mechanism is mechanically coupled to move the second motion generating mechanism and the attachment arm about the first pivot while the second motion generating mechanism is mechanically coupled to move the attachment arm about the second pivot;

an implement attached to a distal end of the attachment arm; and a tremor tracking module ("TTM") attached to the housing to detect motion of the housing, and to generate a first motion signal and a second motion signal that respectively drive the first motion generating mechanism in a first degree of freedom and the second motion generating mechanism in a second degree of freedom to stabilize motion of the implement based on the detected motion of the housing.

2. The handheld tool of claim 1, wherein the first motion generating mechanism comprises a first gearing unit at the first pivot and the second motion generating mechanism comprises a second gearing unit at the second pivot.

3. The handheld tool of claim 2, wherein the first motion generating mechanism comprises a first actuator, a first gear reduction unit coupled with the first actuator, and the first gearing unit driven by the first actuator through the first gear reduction unit to move the implement perpendicular to an orientation of the first actuator, and wherein the second motion generating mechanism comprises a second actuator, a second gear reduction unit coupled with the second actuator, and the second gearing unit driven by the second actuator through the second gear reduction unit to move the implement perpendicular to an orientation of the second actuator.

4. The handheld tool of claim 3, wherein the first actuator is disposed within, and aligned parallel to, the housing, and wherein the second actuator is disposed within the attachment arm, and aligned parallel to, the attachment arm.

5. The handheld tool of claim 1, wherein the first motion generating mechanism moves the implement in the first degree of freedom and the second motion generating mechanism moves the implement in the second degree of freedom to stabilize motion of an implement in 360 degrees as a result of high amplitude motion of the housing, wherein the high amplitude motion comprises user tremor motions having a range of at least 2 centimeters.

6. The handheld tool of claim 5, wherein the first motion generating mechanism moves the implement in the first degree of freedom in a first range up to 10 centimeters and the second motion generating mechanism moves the implement in the second degree of freedom in a second range up to 10 centimeters.

7. The handheld tool of claim 1, further comprising:
at least two sensors, coupled with the TTM, wherein at least a first sensor of the at least two sensors detects high amplitude tremor motions of the housing, the at least two sensors detect relative motions of the housing and the attachment arm, and the at least two sensors provide the detected high amplitude tremor motions and the relative motions to the TTM.

8. The handheld tool of claim 7, wherein the at least two sensors comprise a first inertial measuring unit and a second inertial measuring unit.

9. The handheld tool of claim 8, wherein the flexible sleeve is impermeable to moisture and comprises one of a silicon sleeve, a plastic sleeve, or a rubber sleeve.

10. The handheld tool of claim 1, further comprising:
a flexible sleeve attached to the housing and the attachment arm, wherein the flexible sleeve seals a portion of the handheld tool between the housing and the attachment arm, and wherein the portion contains the first motion generating mechanism and the second motion generating mechanism.

11. The handheld tool of claim 1, wherein the implement comprises any of a manufacturing tool, a surgical tool, a kitchen utensil, a sporting tool, a yard tool, a grooming tool, or a dental hygiene tool.

12. The handheld tool of claim 1, further comprising:
a controller coupled to the TTM to read data indicative of the detected motion;
a memory unit coupled to the controller; and
logic executable by the controller that when executed by the controller causes the handheld tool to perform operations comprising:
generating a motion log within the memory unit based upon the data indicative of the detected motion while a user is holding the handheld tool; and
periodically communicating the motion log to a remote server.

13. The handheld tool of claim 1, wherein the first and second motion generating mechanisms have outputs oriented end-to-end facing each other and the first and second motion generating mechanisms are positioned in-line and parallel with each other and the housing when driven to a center position.

14. The handheld tool of claim 1, wherein the first and second pivots are both disposed between the first and second motion generating mechanisms.

15. The handheld tool of claim 1, wherein the housing has an exterior surface shaped as a handle for holding with a hand and wherein the first motion generating mechanism is disposed entirely within the housing.

* * * * *